(12) United States Patent
Hasegawa

(10) Patent No.: US 7,777,891 B2
(45) Date of Patent: Aug. 17, 2010

(54) ELASTICITY AND VISCOSITY MEASURING APPARATUS

(75) Inventor: Takemi Hasegawa, Yokohama (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 142 days.

(21) Appl. No.: 12/067,439

(22) PCT Filed: Sep. 20, 2006

(86) PCT No.: PCT/JP2006/318573

§ 371 (c)(1),
(2), (4) Date: Nov. 24, 2008

(87) PCT Pub. No.: WO2007/034802

PCT Pub. Date: Mar. 29, 2007

(65) Prior Publication Data

US 2009/0073453 A1 Mar. 19, 2009

(30) Foreign Application Priority Data

Sep. 20, 2005 (JP) ............................. 2005-272495

(51) Int. Cl.
G01B 9/02 (2006.01)
(52) U.S. Cl. .................................................... 356/485
(58) Field of Classification Search ................. 356/450, 356/477, 484, 485
See application file for complete search history.

(56) References Cited

U.S. PATENT DOCUMENTS

| 5,187,147 A | 2/1993 | Ng et al. |
| 5,592,085 A | 1/1997 | Ehman |
| 6,687,625 B2 * | 2/2004 | Srinivasan et al. ............. 702/42 |
| 6,731,967 B1 * | 5/2004 | Turcott ........................ 600/407 |
| 6,879,155 B2 | 4/2005 | Ehman et al. |
| 7,148,970 B2 * | 12/2006 | de Boer ........................ 356/497 |

(Continued)

FOREIGN PATENT DOCUMENTS

| JP | 05-267798 A | 10/1993 |
| WO | WO-2004/040241 A1 | 5/2004 |
| WO | WO-2004/106971 A1 | 12/2004 |

OTHER PUBLICATIONS

G.B. Rouse et al., Brillouin spectra of mixed alkali glasses, Journal of Non-Crystalline Solids, vol. 45, No. 2, 1981, p. 257-269.

H. Xia et al. Vibrational excitations in thin films studied by spatial dispersion Brillouin spectroscopy, Physical Review B, Vo. 54, No. 24, Dec. 15, 1996, p. 17805-17811.

(Continued)

Primary Examiner—Patrick J Connolly
(74) Attorney, Agent, or Firm—Global IP Counselors, LLP

(57) ABSTRACT

Brillouin scattered light is used to measure the distribution of elasticity and viscosity in a measurement object without contact and in a noninvasive and simpler manner. Measuring light emitted from a light source is directed from a light probe onto a measurement object, and scattered light is received by the light probe. A control computer analyzes the light spectrum of scattered light received by the light probe, calculates at least one parameter selected from the center frequency and the linewidth of the elastic wave scattered components as viscoelastic information, matches the viscoelastic information with the position of a target area in the measurement object, and outputs image information. The position information of the target area in the measurement object is acquired by photographing light spots of guide light with a camera provided to the light probe.

9 Claims, 14 Drawing Sheets

U.S. PATENT DOCUMENTS

| | | | | |
|---|---|---|---|---|
| 7,355,716 | B2* | 4/2008 | de Boer et al. | 356/479 |
| 7,567,349 | B2* | 7/2009 | Tearney et al. | 356/479 |
| 7,630,083 | B2* | 12/2009 | de Boer et al. | 356/479 |
| 7,643,152 | B2* | 1/2010 | de Boer et al. | 356/497 |
| 7,720,526 | B1* | 5/2010 | Modell | 356/477 |
| 2009/0073432 | A1* | 3/2009 | Jalali et al. | 356/301 |
| 2009/0073453 | A1* | 3/2009 | Hasegawa | 356/477 |

OTHER PUBLICATIONS

M. Ishihara et al., Viscoelastic characterization of biological tissue by photoacoustic measurement, Jpn J. Appl. Phys., vol. 42, 2003, pp. L556-558.

J. M. Schmitt, OCT elastography: imaging microscopic deformation and strain of tissue, Opt. Exp., vol. 3, 1998, pp. 199-211.

S. J. Randall et al., The measurement and interpretation of Brillouin scattering in the lens of the eye, Proc. R. Soc. Lond., B214, 1982, pp. 449-470.

K. Hattori et al., Light beating spectroscopy of Brillouin scattering in solid polymer, Jpn J. Appl. Phys., 33, 1994, pp. 3217-3219.

T. Horiguchi et al., Development of a distributed sensing technique using Brillouin scattering, J. Lightwave Techno., vol. 13, 1995, pp. 1296-1302.

* cited by examiner (a) Measuring light (b) Scattered light (c) Local-oscillated light (b) Scattered light (c) Local-oscillated light (b) Scattered light (c) Local-oscillated light

FIG. 14

Corneal MPE for direct exposure
of laser radiation [J/m²]

| Wavelength λ [nm] \ Exposure period [s] | ~1.0e-9 | 1.0e-9 ~ 1.8e-5 | 1.8e-5 ~ 5.0e-5 | 5.0e-5 ~ 1.0e-3 | 1.0e-3 ~ 1.0e+1 |
|---|---|---|---|---|---|
| 400 ~ 700 | 5e-3 | | 18 * t^3/4 | | |
| 700 ~ 1050 | 5e-3 * C4 | | 18 * t^3/4 * C4 | | |
| 1050 ~ 1150 | 5e-2 | | | 90 * t^3/4 | |

ELASTICITY AND VISCOSITY MEASURING APPARATUS

FIELD OF THE INVENTION

The present invention relates to an apparatus for measuring the elasticity and viscosity of a measurement object.

BACKGROUND OF THE INVENTION

U.S. Pat. Nos. 5,592,085 and 6,879,155 disclose methods for measuring the elasticity and viscosity distribution of the interior of a measurement object and displaying the measurements as an image by applying pressure waves to the measurement object from the exterior and using magnetic resonance imaging (MRI) to measure the displacement induced by the pressure waves that reach the interior. U.S. Pat. Nos. 5,187,147 and 6,687,625 disclose methods for measuring the elasticity distribution of a measurement object and displaying the measurements as an image by applying pressure to the measurement object from the exterior and using ultrasonic echoes to measure the displacement induced by the pressure that reaches the interior.

When acoustical waves are produced by irradiating one side of a measurement object with pulse light and causing the measurement object to absorb the pulse light energy, the acoustical waves are reflected by the two opposing end surfaces of the measurement object and travel back and forth within the measurement object. Jpn. J. Appl. Phys., Vol., 42, pp. L556-L558 (2003) describes a technique for finding the viscosity-to-elasticity ratio of a measurement object by detecting the energy of the acoustical waves as a function of time in the other side. Opt. Exp., Vol. 3, pp. 199-211 (1998) describes a method for measuring the elasticity distribution of a measurement object and displaying the measurement as an image by applying pressure to the measurement object from the exterior and using optical coherence tomography (OCT) to measure the displacement induced by pressure that reaches the interior.

Another known method is to measure the elasticity and viscosity of a measurement object by Brillouin light scattering. J. Randall and J. M. Vaughan, Proc. R. Soc. Lond., B214, pp. 449-470 (1982) describes a technique for achieving the necessary resolution of 100 MHz or less for Brillouin scattering spectroscopy and removing noise caused by elastic scattering, by using a fragment of biological tissue as the object of measurement and using connected etalons as a high-resolution variable light filter to disperse the scattered light. K. Hattori, et al., Jpn. J. Appl. Phys., 33, pp. 3217-3219 (1994) describes a method which is measuring a polymer as the object and which optical heterodyne detection is used. T. Horiguchi, et al., J. Lightwave Technol., 13, pp. 1296-1302 (1995) describes a technique which is measuring an optical fiber as an object and in which the distribution of a Brillouin frequency shift is measured along the longitudinal direction of the optical fibers.

DISCLOSURE OF THE INVENTION

Problems the Invention is Intended to Solve

With conventional methods, it has been difficult to measure the elasticity and viscosity of a measurement object without contact and in a noninvasive and simple manner. To irradiate a measurement object with ultrasonic waves and to detect ultrasonic waves from the measurement object in an ultrasonic diagnosis, either an ultrasonic probe must be brought into contact with the measurement object, or an ultrasonic transmission medium (water, grease, or the like) must be brought into contact with the measurement object. When MR (magnetic resonance) is used, the measurement object is exposed to electromagnetic waves in a strong magnetic field of about 1 T (tesla), and faint electromagnetic waves emitted by the measurement object are detected. Measurement is therefore difficult in cases in which the measurement object contains magnetic material or electrically conductive material, and the room in which the apparatus is placed must be electromagnetically shielded, which requires bulky equipment. With acoustooptic methods, the shape of the measurement object is limited because one surface of the measurement object is irradiated with laser light while acoustical waves are measured on the opposing surface. With OCT (optical coherence tomography), non-contact measurement is not possible even though this method involves optical measurement, because stress must be applied to the surface of the measurement object. Furthermore, the manner in which the stress applied to the surface is internally attenuated is compensated for by estimation, resulting in large errors.

In the method described in Proc. R. Soc. Lond., B214, pp. 449-470 (1982), received light has low power because the light is dispersed by an optical filter, and there is an upper limit on the power of exciting light to induce scattering due to optical damage in biological tissues. Therefore, a photomultiplier tube must be used as a light-receiving element, and the measurement time must be about 10 minutes despite the undistributed nature of the measurement. The problem with measurement time is essential in light dispersion with an optical filter. When this method is used to create image information, the time needed for two-dimensional scanning is several hundred times longer, and is impractical.

The optical heterodyne detection described in Jpn. J. Appl. Phys., 33, pp. 3217-3219 (1994) allows measurements to be performed in a short time because a high frequency resolution is obtained due to electronic dispersion of light, and noise other than shot noise can be reduced by interference with locally oscillated light having sufficiently high power. However, since there is no device is provided for obtaining position information in the target area, it is difficult to apply this method to biological or other movable measurement objects. Furthermore, light must be inputted and outputted on both sides of the measurement object because of a small scattering angle of 0.97 to 4.96°, which also makes it difficult to apply this method to organisms. Therefore, the shape of the measurement object is restricted, and it is difficult to measure a spatial distribution.

In the method described in J. Lightwave Technol., 13, pp. 1296-1302 (1995), since the measurement object is limited to an optical fiber, only a one-dimensional distribution can be measured, and in order to measure an measurement object distributed in two or more dimensions, optical fibers must be set up on the object and only indirect elasticity information can be obtained.

Thus, Brillouin light scattering has conventionally been performed using a fragment of biological tissue, a polymer, or an optical fiber as an object of measurement, and could not provide image information.

SUMMARY OF THE INVENTION

An object of the present invention is to provide a measurement apparatus and a measurement method whereby Brillouin light scattering can be used to measure the distribution of the elasticity and viscosity of a measurement object without contact and in a noninvasive and simple manner.

Means for Solving these Problems

The elasticity and viscosity measuring apparatus according to the present invention comprises excitation light generating means for generating modulated excitation light; an optical system for focusing the excitation light to a focusing position on a measurement object and capturing scattered light generated by the measurement object; locally oscillated light generating means for generating locally oscillated light; multiplexing means for multiplexing the captured scattered light and locally oscillated light; optical detection means for photoelectrically converting the multiplexed light and generating a photoelectric current; a filter for selecting and extracting a part of an AC component of the photoelectric current; frequency-selective power detection means for selecting and measuring, based on the electric power of the extracted photoelectric current, a frequency component related to modulating the excitation light; and analyzing means for calculating the light spectrum of the scattered light and obtaining at least one parameter selected from the strength of the scattered light, the frequency, and the linewidth based on the elastic waves in the measurement object; wherein the optical system selects and captures a part of the scattered light that forms an angle of 90 degrees or greater in relation to the wave vector of the excitation light.

According to the present invention, position information for the target area is acquired, and the elasticity or viscosity of the measurement object can be imaged. There is less damage to the measurement object than in conventional apparatuses that require compression or contact with an elastic wave transducer. The use of optical heterodyne detection can shorten the time of measuring the spectrum to less than a conventional Brillouin scattered light measurement that uses an optical filter. Optical heterodyne detection also makes it practically possible to acquire image information by measuring spectra in multiple target areas.

EFFECTS OF THE INVENTION

According to the present invention, Brillouin light scattering can be used to measure the distribution of the elasticity and viscosity of a measurement object as image information without contact and in a simple and noninvasive manner.

BRIEF DESCRIPTION OF DRAWINGS

FIG. 14 A table showing corneal MPE;

DETAILED DESCRIPTION OF THE INVENTION

Embodiments of the present invention are described hereinbelow with reference to the diagrams.

Figure 1:
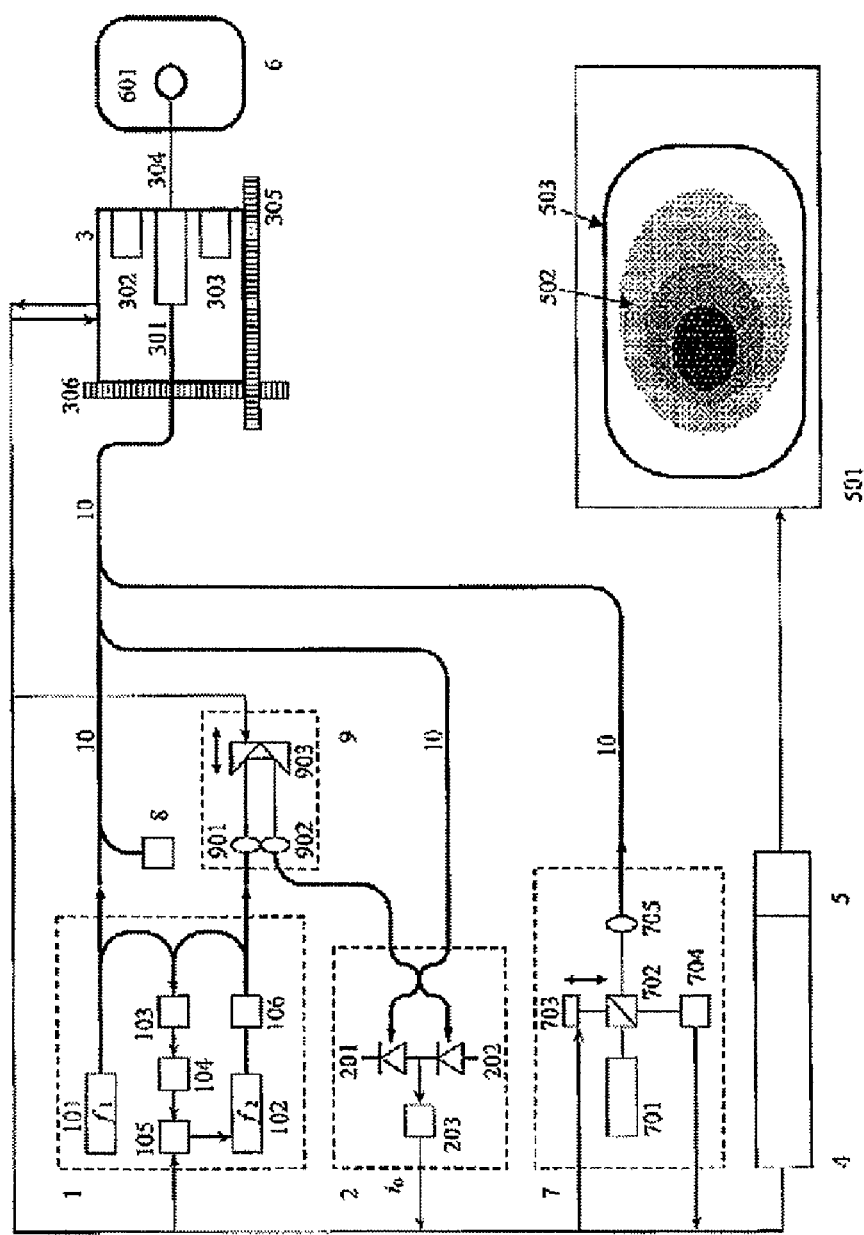
FIG. 1 A schematic view showing an embodiment of the measurement apparatus according to the present invention.

FIG. 1 is a schematic view showing an embodiment of the measurement apparatus according to the present invention. This measurement apparatus comprises a light source 1, an optical heterodyne detector 2, a light probe 3, a control computer 4, an image information display device 5, an optical coherence tomography 7, a guide laser light source 8, and a variable light delay device 9. The light probe 3, the light source 1, the optical heterodyne detector 2, and the optical coherence tomography 7 are connected by optical fibers 10. The locally oscillated light from the light source 1 is directed onto the optical heterodyne detector 2 via the variable light delay device 9. The control computer 4 has a function for controlling the operations of all the components of the apparatus, as well as a function for analyzing the spectrum of received scattered light.

The light source 1 emits measuring light and locally oscillated light whose frequency difference is controlled, and irradiates a measurement object 6 with measuring light via the light probe 3. The scattered light produced by the measurement object scattering the measuring light is integrated with the locally oscillated light via the light probe 3 and is directed to the optical heterodyne detector 2. The control computer 4 finds the center frequency and linewidth of the Brillouin scattered components by analyzing the spectrum of the scattered light. The center frequency of the Brillouin scattered components depends on elasticity, and the linewidth depends on viscosity, and information about the elasticity and viscosity in the target area can therefore be obtained from this measurement. The control computer 4 formulates as image information the information about elasticity and/or viscosity obtained by the spectrum analysis, and outputs this information to the image information display device 5.

The light source 1 outputs two beams of light from separate ports, one for measuring light having frequency $f_1$ and one for locally oscillated light having frequency $f_2$. The measuring light is emitted by a laser light source 101, and the locally oscillated light is emitted by a variable-frequency laser light source 102. The measuring light and the locally oscillated light are integrated and are photoelectrically converted by a photodiode 103, an electric signal is inputted to a frequency measuring instrument 104 to measure the difference in frequency between the measuring light and the locally oscillated light, an error signal indicating an error between the measured value and the value designated by the control computer 4 is created by a frequency control circuit 105, and feedback is supplied to the variable-frequency laser light source 102. This light source reduces noise because the two lasers that supply measuring light and locally oscillated light each oscillate at a single frequency.

The laser light source 101 and the variable-frequency laser light source 102 are capable of producing light of a narrower linewidth than the Brillouin gain linewidth of the measurement object (typically about 100 MHz). The Brillouin gain spectrum can thereby be prevented from being over-evaluated due to the effects of the light source linewidth. The variable-frequency laser light source 102 for locally oscillated light has a more precise frequency than the Brillouin gain linewidth. This light source is preferably a laser diode or a fiber DFB laser having a diffraction grating as an external resonator. Preferably, a polarization state of the locally oscillated light is randomized by a polarization scrambler 106, which is well known in conventional practice. In optical heterodyne detection, fluctuations in the interference components caused by relative fluctuations in polarization between scattered light and locally oscillated light can be prevented from adversely affecting the detection performance.

The frequency of the measuring light is preferably 180 to 750 THz (a wavelength of 400 to 1700 nm in a vacuum). With this configuration, in cases in which a measurement object is an organism or organically derived material, light loss becomes small and a deep part of the object can be measured. This is applicable to diagnosing a lesion such as a tumor or arteriosclerosis. Particularly preferable is a frequency of 250 to 500 THz (a wavelength of 600 to 1200 nm in a vacuum). For example, it is possible to obtain light wherein $f_1$ is 283 THz (1060 nm) by using a Yb-doped fiber laser, and to obtain light wherein $f_1$ is 375 THz (800 nm) by using a laser diode equipped with an external resonator.

The measuring light with the frequency $f_1$ is guided to the light probe 3 via the optical fibers 10, then is emitted through a lens 301 and is directed to a target area 601 of the measurement object 6, whereupon light scattering in the measurement object creates scattered light 304. This scattered light is captured by the lens 301 and coupled to the optical fibers 10, and is then guided to the optical heterodyne detector 2.

Figure 2:
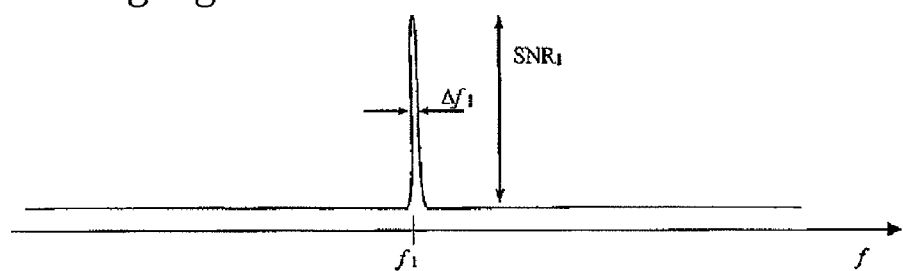
FIG. 2 A pattern diagram showing the frequency spectra of measuring light, scattered light, and locally oscillated light.
Figure 2:
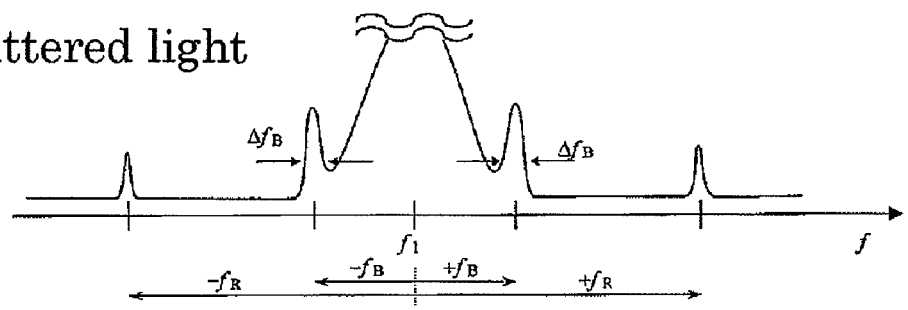
Figure 2:
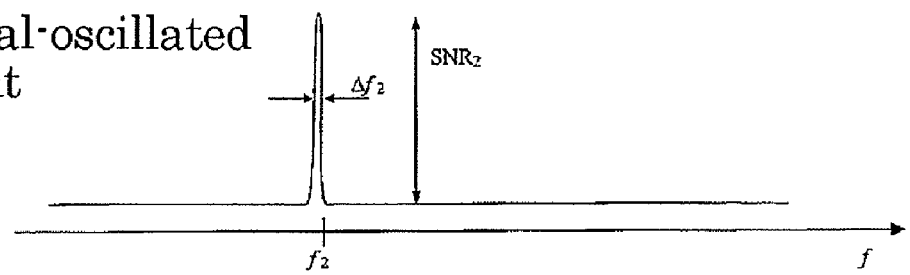

FIG. 2 is a diagram that schematically depicts the frequency spectra of measuring light, scattered light, and locally oscillated light. FIG. 2(a) shows the spectrum of measuring light, FIG. 2(b) shows the spectrum of scattered light, and FIG. 2(c) shows the spectrum of locally oscillated light. Light scattering is described, for example, in Robert W. Boyd, "Nonlinear Optics," Academic Press (1992) Section 7.1, 7.3; and other publications. Scattered light has elastically scattered components at the frequency $f_i$, Brillouin scattered components at $f_1 \pm f_B$, and Raman scattered components at $f_1 \pm f_R$. Elastically scattered components result not only from Rayleigh scattering caused by entropy fluctuations in the measurement object, but also from scattering caused by a nonuniform refractive index in an organism or the like, while Brillouin scattering results from elastic waves in the measurement object, and Raman scattering results from molecular vibration in the measurement object. The frequency shift $f_B$ in Brillouin scattering is given by the formula:

$$f_B = (2nv_a/\lambda)\sin(\theta/2) \quad (1)$$

wherein n is the refractive index, $\lambda = c/f_1$ (c being the speed of light in a vacuum) is the light wavelength in a vacuum, $v_a$ is the propagation speed of elastic waves, and $\theta$ is the scattering angle (the angle formed by the wave vectors of measuring light and scattered light). The spectral width $\Delta f_B$ is given by the formula:

$$\Delta f_B = \{8\pi n^2/(\rho\lambda^2)\} * \{(4/3)\eta_s + \eta_b\}\sin^2(\theta/2) \quad (2)$$

wherein $\rho$ is the medium density, $\eta_s$ is the shearing viscosity, and $\eta_b$ is the bulk viscosity. The spectral width $\Delta f_B$ is proportionate to the inverse of the lifetime $\tau_B$ of acoustical waves, and can also be given by $\Delta f_B = 1/(2\pi\tau_B)$.

The signal to noise ratios $SNR_1$ and $SNR_2$ of measuring light and locally oscillated light are preferably 40 dB or greater, whereby the effects of noise caused by elastic scattering can be reduced. More specifically, the ratios are preferably 160 dB/Hz or greater. At this time, the optical noise is −80 dB in the 100 MHz band, which is a typical Brillouin linewidth. Since organic tissues have strong elastic scattering, it is vital that the measuring light and locally oscillated light have low optical noise. N. Berovic, et al., Eur. Biophys. J. Vol. 17, pp. 69-74 (1989) states that elastic scattering in muscle fibers and other organic tissues is about 70 dB stronger than Brillouin scattering. The noise in the measurement of Brillouin scattered light is caused by interference between elastically scattered measuring light noise and locally oscillated light, and the interference between elastically scattered measuring light and locally oscillated light noise. However, keeping the noise light at −80 dB or less as described above causes the effects of elastic scattering to be equal to or less than the Brillouin scattering signal, and makes it possible to prevent the SN ratio from being reduced by elastic scattering.

Figure 3:
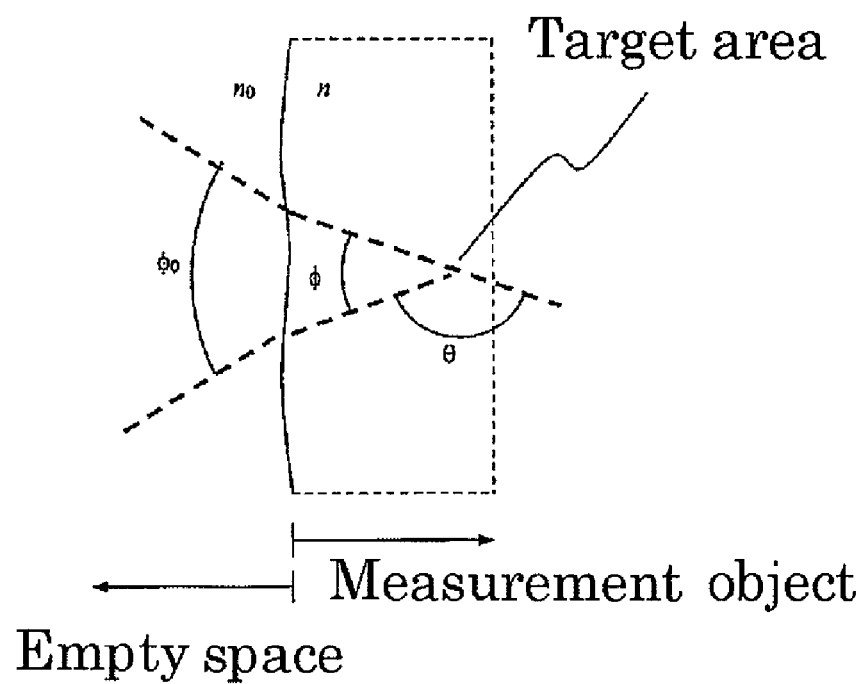
FIG. 3 A diagram showing the manner in which measuring light and scattered light is diffracted.
Figure 4:
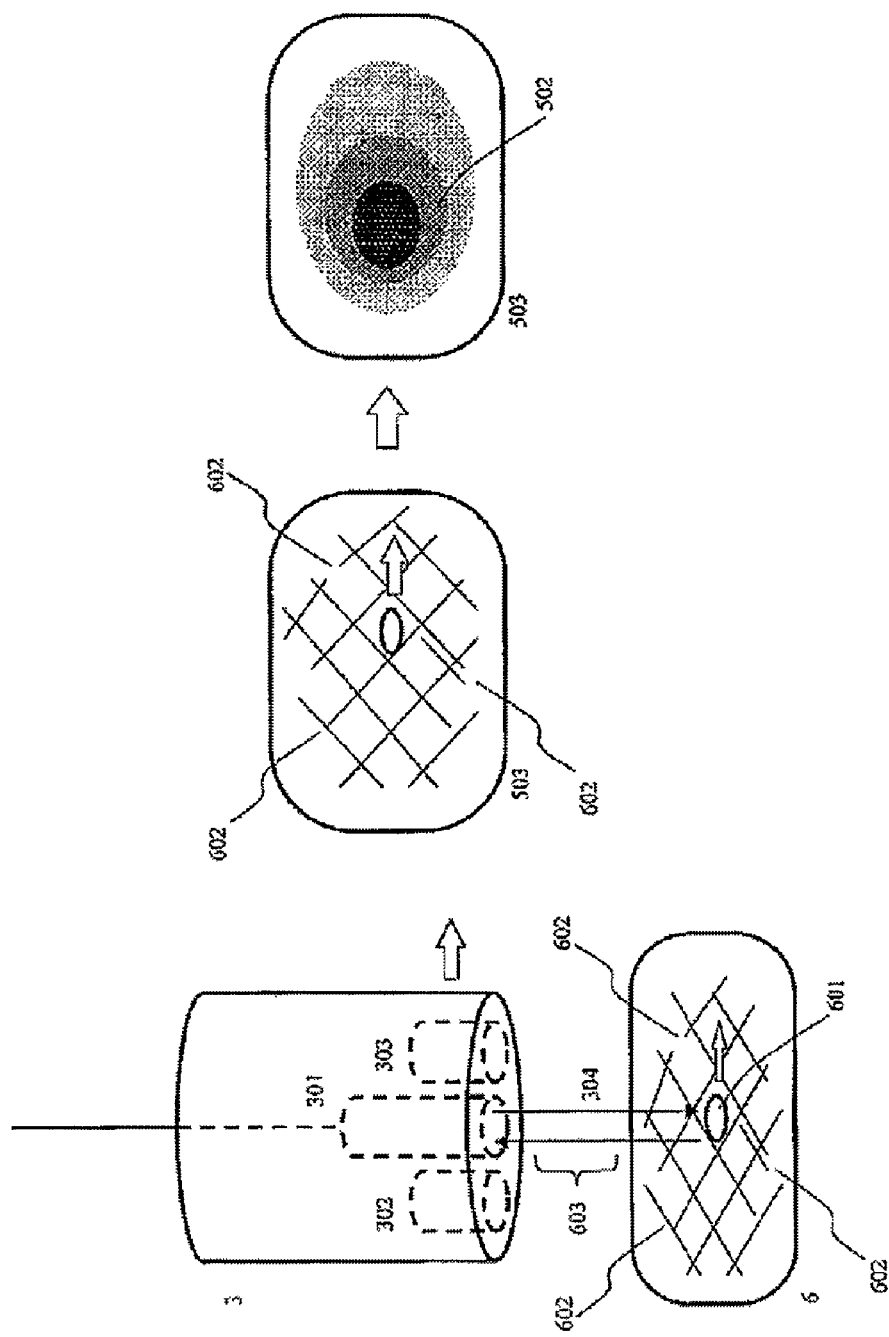
FIG. 4 A diagram showing an example of a light probe.
Figure 10:
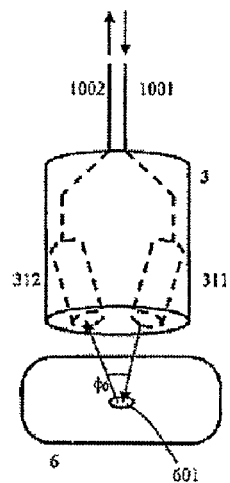
FIG. 10 A diagram showing another example of a light probe.

The scattering angle $\theta$ is found by the law of refraction. This angle is given by the formula:

$$f_B = (2v_a/\lambda)\{n^2 - n_0^2 \sin^2(\phi_0/2)\}^{1/2} \quad (3)$$

wherein $\phi_0$ is the supplementary angle to the angle formed by the measuring light and scattered light in the external boundary of the measurement object, as shown in FIG. 3. The velocity $v_a$ is expressed by $v_a = (c_{11}/\rho)^{1/2}$, using the first row and first column element $c_{11}$ of an elastic matrix. The scattering angle in the light probe shown in FIGS. 1 and 4 is $\theta = 180°$, and $\phi_0 = 0°$. In the light probe shown in FIG. 10, the angle is $\theta < 180°$, and $\phi_0 > 0°$. When this type of light probe is used, it is possible to input and output light to the measurement object on only one side, and the measurement object can therefore be an organism that could not have been measured with conventional techniques wherein light is inputted and outputted on both sides. When the light probe shown in FIG. 10 is used, distribution in the depth direction can be measured.

Therefore, by acquiring information about the light wavelength, scattering angle, and refractive index in advance, and by measuring the frequency shift or linewidth of Brillouin scattering, information about the elasticity and viscosity in the target area can be obtained. Furthermore, the distribution of elasticity and viscosity can be imaged by measuring the elasticity and viscosity in multiple target areas and matching them with position information. The distribution may also be imaged by matching the frequency shift or linewidth with position information instead of the elasticity and viscosity. The hardness of an organism has a correlation to tissue fibrosis and other pathological information, but the absolute values of elasticity and viscosity are not absolutely necessary to obtain this type of pathological information, and it is often sufficient to merely know the relative difference from the surrounding healthy areas. In such cases, imaging the frequency shift or linewidth has the advantage of simplifying data processing.

In the measuring apparatus of the present invention, the light probe has the mechanism for obtaining the position information necessary for imaging. The guiding light emitted by the guide laser light source 8 integrates with the measuring light and propagates through the same optical fibers, and is emitted onto the target area 601 via the light probe 3. The spot of guiding light on the target area 601 is photographed by a camera 302 provided to the light probe 3, as shown in FIG. 4. Furthermore, the camera photographs an image of the measurement object including the periphery of the target area 601, and measures the position of the spot of guiding light using characteristic regions 602 of the measurement object as references. The position information of the target area 601 is thereby obtained. Illumination 303 may be used to photograph an image of the measurement object 6, whereby position information can be acquired in a dark spot under an endoscope or the like. Furthermore, measurements can be taken while moving the light probe 3 along the surface of the measurement object, and distribution information can be formulated by matching the viscoelasticity measurement results with the position information. The formulated distribution information about elasticity and viscosity is superposed over the image 503 of the measurement object photographed by the camera, and is displayed on an image display device 501 as an elasticity-viscosity distribution image 502 expressed in hue or shading. In this case, when the measurement object contains movement, characteristic movement can be detected to remove the effects of movement from the measurement.

This method for obtaining position information using the characteristic regions 602 of the measurement object as references has an advantage in that the movement of the measurement object can be followed, and this method is suitable for measuring organisms and the like having a pulse. The characteristic regions 602 are preferably selected so as to form a vertex of a triangle containing the target area 601, whereby effective compensation can be made for movement in cases in which movement in the measurement object is spatially nonuniform. The wavelength of the guiding light is preferably a wavelength to which the camera is sensitive; for example, the camera is preferably a widely used CCD camera and the guiding light source is preferably a laser diode having a wavelength of 630 nm. A camera sensitive to the wavelength of the measuring light, such as an infrared camera, for example, may be used, and the measuring light may also fulfill the role of guiding light. An operator of the apparatus may move the light probe by hand, but it is preferable that a mechanism be provided for moving the light probe 3 along rails 305, 306 as shown in FIG. 1, and that a device be provided for measuring the amount of movement, because needless movement can then be eliminated.

Furthermore, there is an empty space 603 between the light probe 3 and the measurement object 6. Therefore, the light probe 3 does not come into direct contact with the measurement object 6. Conventional elasticity diagnostic techniques, whether they use ultrasound, MRI, OCT, or the like, all require contact with the measurement object, but since there is no contact in the present invention, mechanical damage and contamination to the measurement object can be prevented. The empty space may be only air, or may be filled with water or another liquid or gel substance. With a measurement object in which contact is not a problem, the measurements can be taken even if there is no empty space and contact is made.

In the optical heterodyne detector 2, a photoelectric current is created from the interference between the scattered light and the locally oscillated light that has the frequency $f_2$ and is generated by the variable-frequency laser light source 102, and the spectrum of Brillouin scattered components is measured at $f_1+f_B$ or $f_1-f_B$ of scattered light. A balanced diode configuration that uses the difference between photoelectric currents from the two photodiodes 201, 202 is preferably used because the effects of intensity noise can be eliminated. To measure the spectrum of scattered light, a component having the frequency $f_2 \pm f_f$ in the scattered light spectrum can be extracted by passing a photoelectric current through an electric signal filter 203 whose transmissive band is at a frequency $f_f$ of zero or near zero, and a photoelectric current $i_0$ equivalent to this component can be measured as the filter output.

Figure 5:
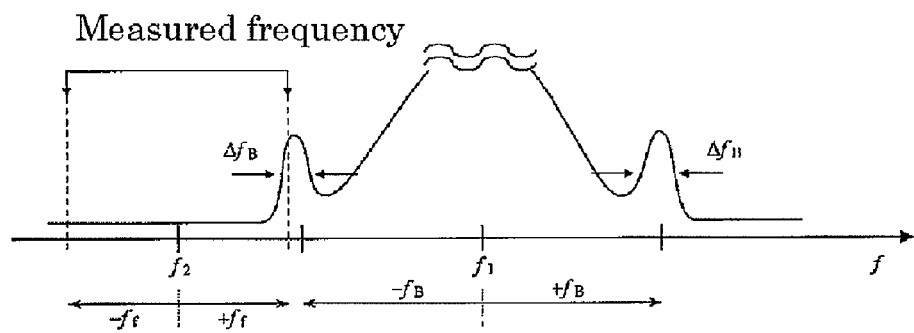
FIG. 5 A diagram showing a method for obtaining a scattered light spectrum.
Figure 5:
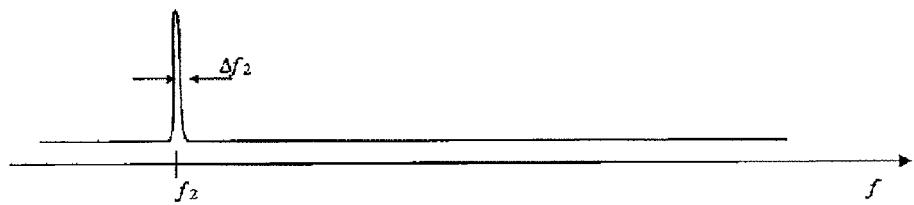

When $f_f$ is selected, which is greater than the linewidth $\Delta f_B$ (about 100 MHz) of Brillouin scattering, and $f_2$ is selected so that $f_2+f_f$ or $f_2-f_f$ is equal to $f_1+f_B$ or $f_1-f_B$, the spectrum of scattered light can be obtained by varying $f_f$ and measuring the photoelectric current $i_0$, as shown in FIG. 5.

Figure 6:
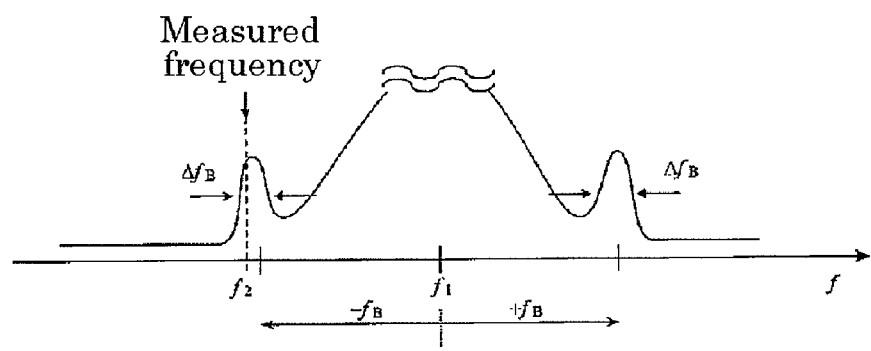
FIG. 6 A diagram showing a method for obtaining a scattered light spectrum.
Figure 6:
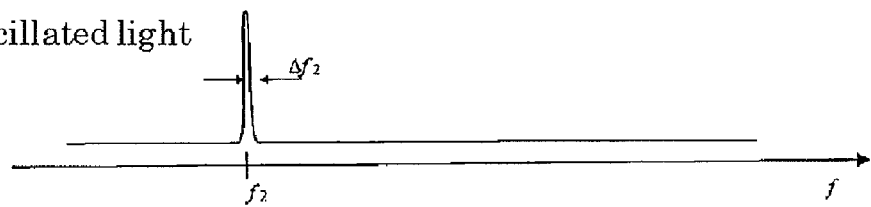

If $f_f$ is 0 and the photoelectric current $i_0$ is measured while varying the frequency difference $\Delta f=f_1-f_2$ as shown in FIG. 6, the spectrum of Brillouin scattered light can be measured at $f_1+f_B$ when $\Delta f<0$, and at $f_1-f_B$ when $\Delta f>0$.

Figure 7:
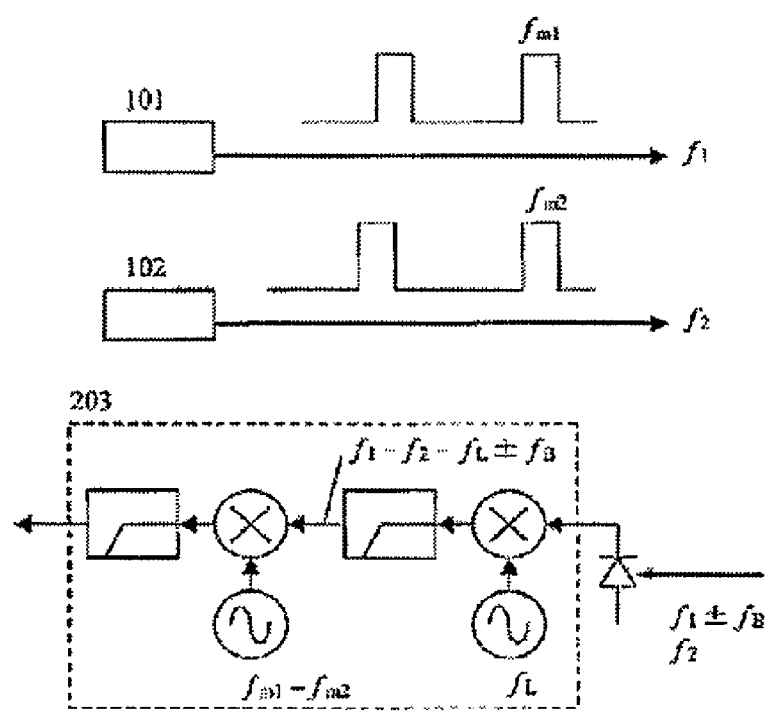
FIG. 7 A diagram showing a method for obtaining a scattered light spectrum.

As shown in FIG. 7, the interference components of locally oscillated light and scattered light can be extracted by using pulse light of repetition frequency $f_{m1}$ as the measuring light (and therefore the scattered light), and pulse light of repetition frequency $f_{m2}$ as the locally oscillated light, and applying a filter having the frequency $|f_{m1}-f_{m2}|$ to the photoelectric current of Brillouin scattered components that have a frequency $+f_B$ or $-f_B$ and are obtained by optical heterodyne detection. With this method, noise resulting from elastic scattering can be reduced in relative terms, and the SN ratio of the measurement can be improved.

Figure 8:
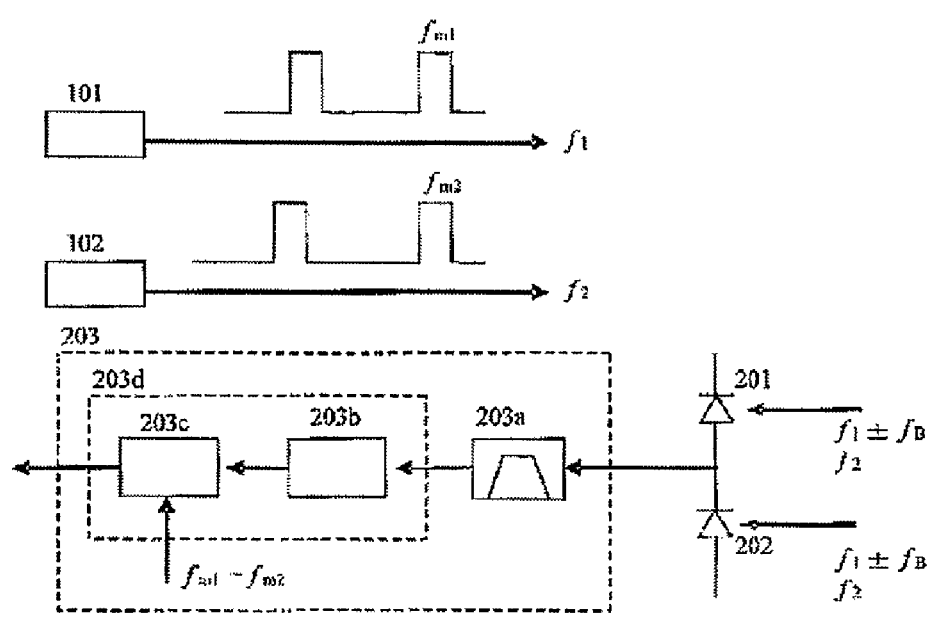
FIG. 8 A diagram showing a method for obtaining a scattered light spectrum.

It is more preferable to use an optical heterodyne detector such as the one shown in FIG. 8. FIG. 8 is a diagram showing the method for obtaining a scattered light spectrum. In FIG. 8, a photoelectric current from the balanced photodiodes 201, 202 is filtered by a band-pass filter 203a having a transmission frequency $f_f$ and a transmissive band $\Delta f_f$ and detected by a square-law detector 203b, and the output of the square-law detector is measured by a lock-in amplifier 203c. The reference frequency of the lock-in amplifier 203c is the frequency difference $|f_{m1}-f_{m2}|$ between the modulation frequency $f_{m1}$ of the measuring light and the modulation frequency $f_{m2}$ of the locally oscillated light, allowing a frequency-selective power detection device 203d to selectively detect power at this frequency. The power of the noise in the lock-in amplifier can be reduced to $(\Delta f_f T)^{-1/2}$ by calculating an integral over time T. Therefore, the noise power N based on local light shot noise, which is the primary cause of noise in optical heterodyne detection, is given by the formula $$N = A P_L h\nu (\Delta f_f T)^{1/2}$$

wherein $P_L$ is the local light power, h is Planck's constant, $\nu$ is the optical frequency, and A is a proportionality constant. The power S of the signal resulting from Brillouin scattered light is given by $$S = A P_L P_B (\Delta f_f / \Delta f_B) \quad (\Delta f_f \leq \Delta f_B)$$
$$= A P_L P_B \quad \text{(otherwise)}$$

wherein $P_B$ is the power of Brillouin scattered light, and $\Delta f_B$ is the linewidth. Therefore, the SN ratio of the measurement is $$SNR = (P_B / (h\nu \Delta f_B)) * (\Delta f_f T)^{1/2} \quad (\Delta f_f \leq \Delta f_B)$$
$$= (P_B / (h\nu \Delta f_f)) * (\Delta f_f T)^{1/2} \quad \text{(otherwise)}$$

Since there is a monotonic increase in $\Delta f_f$ when $\Delta f_f \leq \Delta f_B$, and there is a monotonic decrease in $\Delta f_f$ when $\Delta f_f > \Delta f_B$, the SNR reaches a maximum when $\Delta f_f = \Delta f_B$. Since the Brillouin linewidth of organic tissue is often 10 MHz to 1 GHz, the band $\Delta f_f$ of the band-pass filter is preferably 10 MHz to 1 GHz. Furthermore, it is preferable that the filter band be variable, that the filter band be increased if the measured linewidth is greater than the filter band, and that the filter band be adjusted to a minimum where the measured value of the linewidth does not increase even if the filter band is increased. The filter band and the Brillouin linewidth can thereby be made to coincide, and the SNR can be maximized as described above.

Acoustic velocity in a GHz band in typical organic material is about 1.6 km/s as described in J. M. Vaughan and J. T. Randall, Nature V. 284, pp. 489-491 (1980), for example. Therefore, when the refractive index is about 1.5, the light wavelength is 1.06 μm, and the scattering angle is 170°, the Brillouin frequency shift $f_B$ is about 4.5 GHz. Therefore, the frequency difference Δf between measuring light and locally oscillated light is kept in the vicinity of 4.5 GHz.

Figure 9:
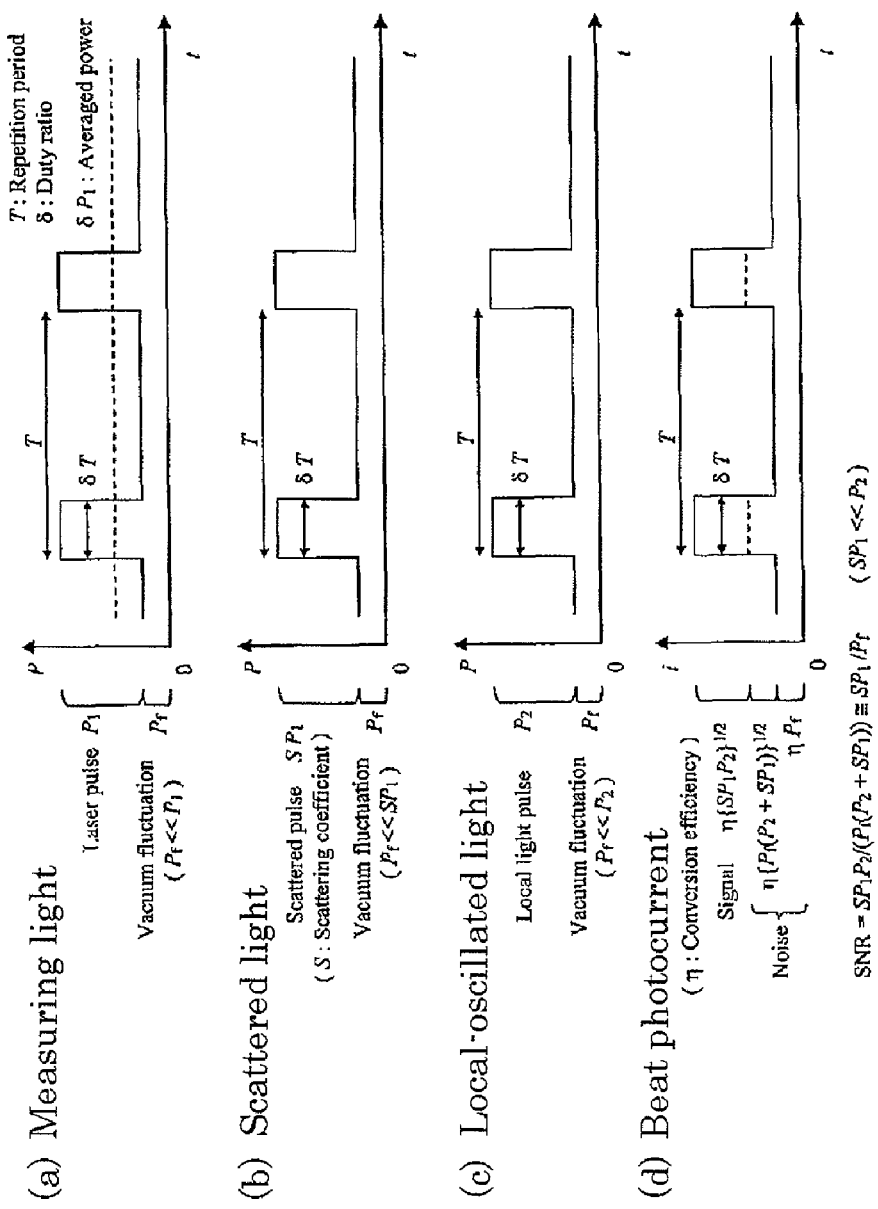
FIG. 9 An explanatory diagram of a case of using pulse light as measuring light and locally oscillated light.

CW light can be used as the measuring light and the locally oscillated light, but it is preferable to use pulse light wherein the cycle and width coincide as shown in FIG. 9. In FIG. 9, the measuring light, scattered light, and locally oscillated light constitute pulse light having a cycle T and a duty ratio δ, and the timing of the pulses of scattered light and locally oscillated light in the optical heterodyne detector are adjusted and made to match by the variable light delay device 9 in FIG. 1. The variable light delay device 9 is composed of collimation lenses 901, 902 and a movable mirror 903. The photoelectric current of the interference components reaches a maximum when the pulse timings coincide and can therefore be adjusted to a maximum. As shown in the system in FIG. 9, the photoelectric current signal in the optical heterodyne detector is the product $SP_1P_2$ of the power of locally oscillated light and the power of scattered light, and the noise is the interference component of the fluctuation $P_f$ in a vacuum and the sum of locally oscillated light and scattered light ($P_2+SP_1$). Therefore, if the pulses do not completely coincide, there is a time duration in which only the locally oscillated light or the scattered light has significant optical power, while only the other fluctuates in a vacuum. The photoelectric current created during this time contains only noise and no signals, and the overall signal to noise ratio is therefore degraded. Therefore, a closer matching of the pulses coincide produces better results. Since the average optical power can be reduced by using pulse light, thermal damage to the measurement object can be prevented. It is also possible to avoid expansion and the like caused by the heat generated by optical absorption in the measurement object. Pulses with a longer duration than the lifetime of the acoustical waves are preferably used because if the duration of the pulses falls below the lifetime of the acoustical waves, scattering efficiency is reduced. The lifetime $\tau_B$ of the acoustical waves is expressed by $\tau_B=1/(2\pi\Delta f_B)$ in accordance with the linewidth $\Delta f_B$ of the Brillouin scattered light, and since $\Delta f_B$ is equal to or greater than 0.45 GHz according to the publications of J. M. Vaughan et. al., the lifetime is preferably 35 ps or greater, and even more preferably 1 ns or greater. The pulse width is preferably 1 ms or less in order to avoid a temperature increase in the target area. The repetition frequency of the pulses is preferably kept at 500 Hz or greater and 500 MHz or less for in order to obtain correspondence with the pulse width, and the inverse of the duty ratio is preferably 2 or greater and $10^6$ or less.

More specifically, the maximum permissible exposure (MPE) stipulated in JIS 6802C can be used as a measure of the power of measuring light that does not cause optical damage to a measurement object. FIG. 14 is a diagram showing the corneal MPE as stipulated in JIS 6802C. In FIG. 14, the correction factor $C_4$ is $10^{0.002(\lambda-700)}$. The MPE for repetitive pulse radiation is determined using the most rigorous of the following requirements a), b), and c).

a) Exposure from any single pulse in a pulse train must not exceed the MPE for a single pulse.

b) The average exposure of a pulse train over a sustained period of pulses must not exceed the MPE shown in FIG. 14 for a single pulse over a sustained period.

c) Exposure from all single pulses in a pulse train must not exceed the MPE for a single pulse multiplied by the correction factor $C_5=N^{-1/4}$ (N: expected number of pulses during exposure).

Figure 15:
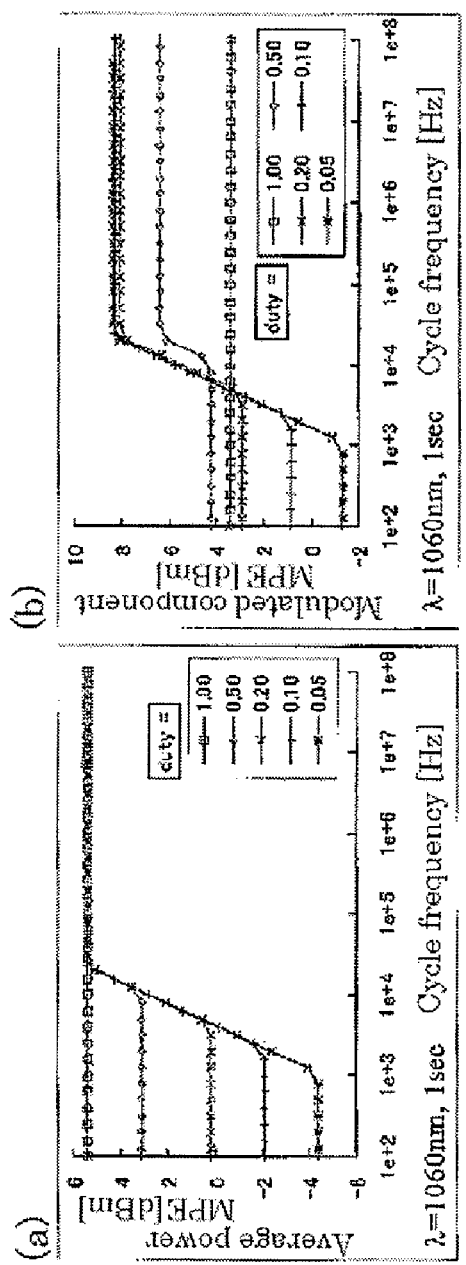
FIG. 15 A graph showing corneal MPE.

The permissible power depends on pulse width and repetition frequency, as shown in FIG. 14. In view of this, a wavelength of 1060 nm and an exposure time of 1 sec were used as typical values to calculate the dependence of MPE on pulse repetition frequency and duty ratio, and the results of these calculations are shown in FIG. 15. A circle 7 mm in diameter is assumed as the exposure area equivalent to the iris. FIG. 15(a) shows the MPE at average power. The upper limit of average power is +5.4 dBm=3.5 mW at a repetition frequency of 30 kHz, regardless of the duty ratio. Since the measuring light is modulated in the present embodiment and a signal synchronized with this modulation is detected, the effective power of measuring light is not the average power, but is a Fourier component in the modulated frequency. FIG. 15(b) shows this as a modulated component MPE. According to FIG. 15(b), the modulated component MPE reaches a maximum of +8.4 dBm when the duty ratio is equal to or less than 0.2 and the repetition frequency is equal to or greater than 30 kHz. Therefore, the measuring light is preferably pulse light wherein the duty ratio is equal to or less than 0.2, the repetition frequency is equal to or greater than 30 kHz, and the average power is equal to or less than 3.5 mW.

The polarization scrambler 106 randomly varies the state of polarization of the locally oscillated light. The fluctuation in the polarization of the scattered light brought about by the fluctuation in the polarization characteristics of the measurement object can thereby prevent the photoelectric currents of the photodiodes (103, 201, 202) from becoming unstable. The polarization of the measuring light may be scrambled. Instead of polarization scrambling, the optical heterodyne detector may have a polarization diversity configuration, whereby optical strength fluctuations and other parasitic phenomena that accompany polarization scrambling can be eliminated.

Figure 16:
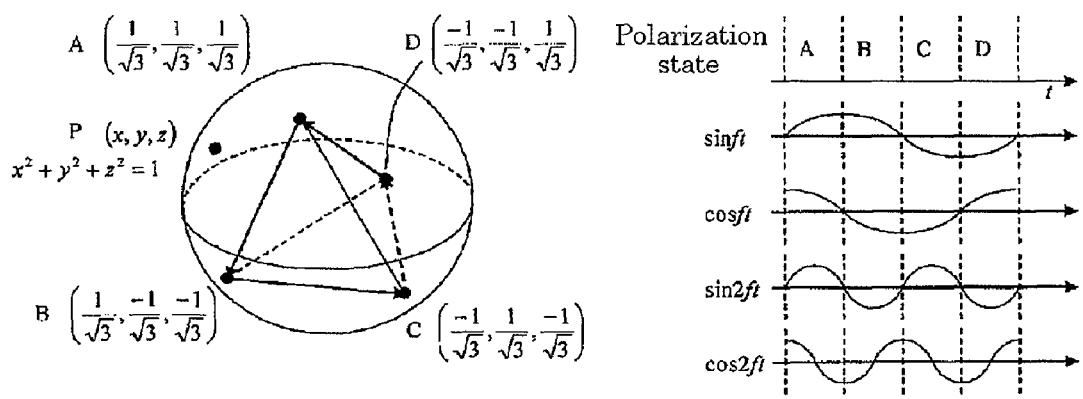
FIG. 16 A diagram showing a system for adjusting polarization.

Furthermore, it is preferable to modulate the polarization of the locally oscillated light at a frequency of $f_{m2}$ instead of modulating the locally oscillated light at a frequency $f_{m2}$ and performing synchronous detection at a frequency difference $|f_{m1}-f_{m2}|$ relative to the modulated frequency $f_{m1}$ of the measuring light, as shown in FIGS. 7 and 8. At this time, as shown in FIG. 16, it is preferable to use a modulation system for the state of polarization in which the four vertices of a tetrahedron in a Poincaré sphere move every ¼ of a cycle, and to measure $(c_1^2+c_2^2)^{1/2}$ using as $c_1$ and $c_2$ the Fourier components of the frequencies $f_{m2}-f_{m1}$ and $2f_{m2}-f_{m1}$. The efficiency K of optical heterodyne detection depends on the correlation between the states of polarization of scattered light and locally oscillated light. Formula (4) is the result of expressing the state of polarization as described in FIG. 16.

[Eq. 1]

$$K = \begin{cases} (x+y+z)/\sqrt{3} & \text{(state of polarization}=A) \\ (x-y-z)/\sqrt{3} & \text{(state of polarization}=B) \\ (-x+y-z)/\sqrt{3} & \text{(state of polarization}=C) \\ (-x-y+z)/\sqrt{3} & \text{(state of polarization}=D) \end{cases} \quad (4)$$

The state of polarization varies in the order A→B→C→D between modulation cycles. Expressing the Fourier component $c_n$ in formula (5) leads to formula (6) and hence formula (7), and output can be obtained that does not depend on the state of polarization of scattered light.

[Eq. 2]

$$c_n = \sqrt{a_n^2 + b_n^2}, \; a_n = 2f \oint \kappa(t)\cos[2\Pi nft]dt, \quad (5)$$

$$b_n = 2f \oint \kappa(t)\sin[2\Pi nft]dt$$

$$a_1 = \frac{4z}{\Pi\sqrt{3}}, \; b_1 = \frac{4x}{\Pi\sqrt{3}}, \; a_2 = 0, \; b_2 = \frac{4y}{\Pi\sqrt{3}} \quad (6)$$

$$\sqrt{c_1^2 + c_2^2} = \frac{4}{\Pi\sqrt{3}} \quad (7)$$

Furthermore, it is possible to bring the AC component of the power of locally oscillated light substantially to zero by modulating a polarization state without modulating the strength of the locally oscillated light. It is therefore possible to use an AC-coupled photoreceiver in which a photodiode and an amplifier are coupled with the alternating currents. Such a receiver can have a higher saturated light input than a DC-coupled receiver, and locally oscillated light with greater power can therefore be used while scattered light can be detected with greater sensitivity.

In FIG. 1, an optical coherence tomography 7 is included as a second optical diagnostic device. This is a device for measuring the spatial distribution of an elastic scattering coefficient of a measurement object. As is well known, light from a superluminescent diode 701, which is a low-coherence light source, is divided by a beam splitter 702 into reference light and light for illuminating the measurement object, and the scattered light from the measurement object is focused by a lens 705 and integrated with the reference light by the beam splitter 702 and caused to undergo interference on a photodiode 704. The local elastic scattering coefficient in the measurement object is thereby measured, and the elastic scattering coefficient is furthermore distributed in the depth direction by varying the length of the optical path of the reference light by using a movable mirror 703. Furthermore, the lateral distribution can be obtained by moving the light probe 3 in a direction that intersects the optical axis. Measuring elastic scattering is significantly different from the present invention in which Brillouin scattering is measured. The measuring light and scattering light of the optical coherence tomography share some of the optical fibers 10 and the light probe 3 as an optical path with the measuring light and scattered light of the present invention. It is thereby possible to achieve a match between the positions of the measurement results obtained by two light-measuring devices. Multiple physical quantities can be diagnosed at one position by integrating a second light-measuring device in this manner. Measuring a group of multiple physical quantities rather than only one physical quantity can reduce the probability of false-positive or false-negative erroneous conclusions, and diseases can be diagnosed with greater precision. Integrating existing optical diagnostic information with the information about elasticity and viscosity newly provided by the present invention makes it possible to detect hardened arteries, tumors, and the like with greater sensitivity, and to determine such problems with greater precision when an organism is the measurement object. It is preferable that an image be displayed of the results of diagnosing the presence or absence and the severity of a disease by combining the measurement results obtained by individual measuring devices, rather than using these results separately.

Instead of an optical coherence tomography, the second measuring device may be another well known measuring device that depends on the intended purpose, such as an image photograph for measuring color or light absorbance of the measurement object, a polarization optical coherence tomography for measuring birefringence, or a fluorescent image photographic device for measuring the fluorescent spectrum. One possible example of integration in a case in which the measurement object is a blood vessel is to integrate the results of diagnosing not only the elasticity of the blood vessel wall, but also the thickness of the endothelial cell layer or smooth muscle cell layer of the blood vessel wall, whereby hardened arteries can be detected with greater sensitivity, and lifestyle-related conditions can be diagnosed more quickly. In cases in which the measurement object is a structure including a border between tumorous cells and healthy cells, integrating the results of measuring not only the elasticity and viscosity of the structure, but also the strength of light scattering as well as fluorescence caused by autofluorescence or biomarkers, makes it possible to distinguish between tumorous structures and healthy structures with greater precision, to reduce tumorous residue after tumor excision or radiation treatment, and to reduce damage and other problems to healthy structures.

The light probe can have other configurations besides the one in FIG. 4. One example is shown in FIG. 10. In the light probe shown in FIG. 10, measuring light and scattered light pass through separate optical paths, and the measuring light passes through an irradiating light-transmitting optical fiber 1001 to be focused onto a target area 601 by a light-irradiating lens 311. Scattered light is captured by a light-capturing lens 312 and is coupled to a scattered light-transmitting optical fiber 1002. The illuminating light-transmitting optical fiber 1001 is coupled to the superluminescent diode 701 and the light source 1 and guide laser light source 8 in FIG. 1; and the scattered light-transmitting optical fiber 1002 is coupled to the optical heterodyne detector 2 and the photodiode 704. In the light probe shown in FIG. 10, scattered light from a position separated by a fixed distance from the light probe 3 can be selectively captured because the angle of the captured scattered light to the measuring light is less than 180°. Therefore, distribution in the depth direction can be measured by taking measurements while varying the distance between the light probe 3 and the measurement object 6. The spatial distribution of viscoelasticity can be measured by measuring scattered light and measuring the amount of movement while moving the light probe 3 along the rails 305, 306 as shown in FIG. 1.

Figure 11:
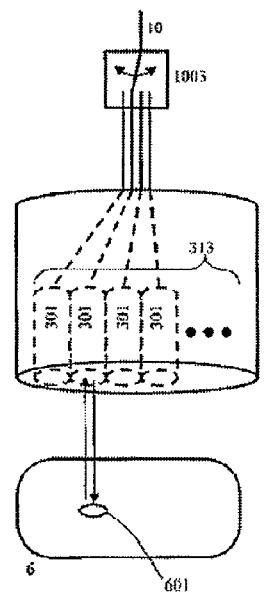
FIG. 11 A diagram showing another example of a light probe.

Another example of a light probe is shown in FIG. 11. The light probe in FIG. 11 is provided with a lens array 313 configured by arraying multiple lenses 301 that direct measuring light and capture scattered light. Furthermore, one lens from among these is selected, and an optical fiber switching device 1003 is used to connect this lens with an optical fiber 10 for transmitting measuring light and scattered light. The spatial distribution of viscoelasticity can be measured by measuring the scattered light while switching the lens with the switching device 1003 and establishing a match with the relative positions between the lenses measured in advance. When this light probe is used, position information can be acquired to formulate image information without moving the light probe. Since the light probe is simplified by omitting the movement mechanism, the light probe can be used in the strong MRI magnetic fields.

Figure 12:
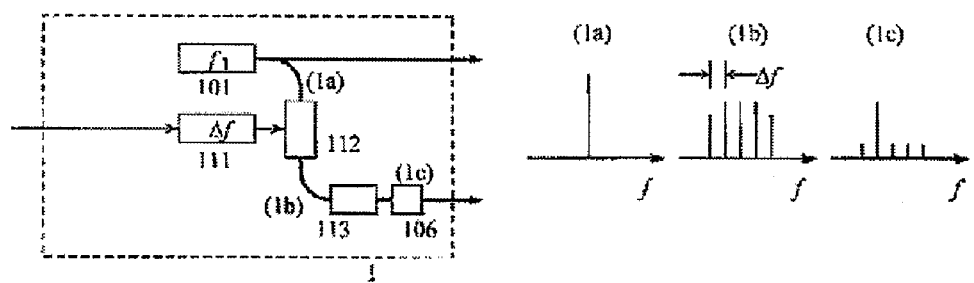
FIG. 12 A diagram showing an example of a laser light oscillator.

The laser light-emitting device can have other configurations besides the one in FIG. 1. One example is shown in FIG. 12. In the laser light-emitting device in FIG. 12, laser light that has frequency $f_1$ and is generated by a laser light source 101 is split in two, and one part of the laser light is used as measuring light. The other is modulated by a light modulator 112 in amplitude, phase, or both with the aid of a high-frequency electrical signal having frequency $\Delta f$. The carrier band ($f_1$) and either the modulation-induced upper sideband ($f_1+\Delta f$) or the modulation-induced lower sideband ($f_1-\Delta f$) are contracted by an optical filter 113, thereby making the spectrum asymmetrical and producing locally oscillated light whose frequency $f_2$ is different from $f_1$. The frequency difference between the measuring light and the locally oscillated light can be varied by varying the frequency $\Delta f$ of a high-frequency generator 111 for generating high-frequency electrical signals as modulated signals, and a function similar to the light source in FIG. 1 can be obtained by randomizing the polarization of the locally oscillated light with the aid of the polarization scrambler 106. The laser light generator is shown in the left-hand part of the diagram, while the spectrum of the positions (1*a*), (1*b*), and (1*c*) in the transmission path of the generator is shown in the right-hand part of the diagram.

Figure 13:
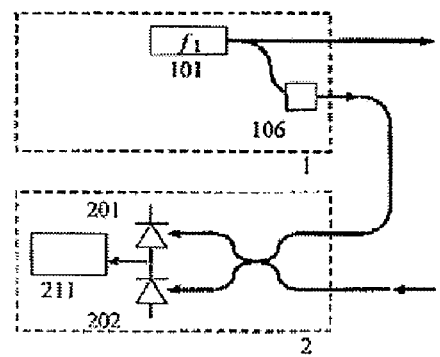
FIG. 13 A diagram showing a structural example of a light source and an optical heterodyne detector.

The light source 1 and the optical heterodyne detector 2 can have the configuration shown in FIG. 13. In this configuration, the laser light generator splits laser light with a frequency $f_1$ in two and outputs measuring light and locally oscillated light. Therefore, the frequency of the locally oscillated light is $f_2=f_1$. The polarization of the locally oscillated light is randomized by the polarization scrambler 106, and the locally oscillated light is used to receive the scattered light with the optical heterodyne detector, whereby a high-frequency electrical signal having a center frequency $f_B$ and a linewidth $\Delta f_B$ is obtained. The spectrum of Brillouin scattered light can be measured by measuring the spectrum of the electrical signal with the aid of a microwave spectrum analyzer 211.

Figure 17:
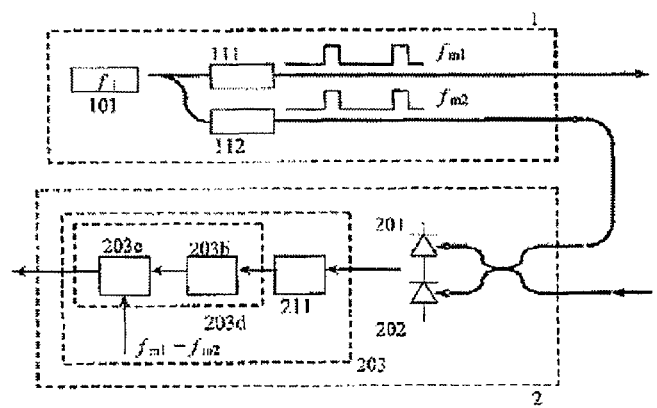
FIG. 17 A diagram showing a structural example of a light source and an optical heterodyne detector.

More preferably, as shown in FIG. 17, measuring light and locally oscillated light are modulated at $f_{m1}$ and $f_{m2}$ by light modulators 111 and 112, photoelectric currents from balanced photodiodes 201, 202 are inputted to a spectrum analyzer 211, the center frequency output is detected by a square-law detector 203*b*, and the component having the frequency $|f_{m1}-f_{m2}|$ in the output is measured by a lock-in amplifier 203*c*. The spectrum analyzer is caused to function as a variable filter by using the center frequency output of the spectrum analyzer as shown in Jpn. J. Appl. Phys., 33, pp. 3217-3219 (1994). The spectrum of scattered light can be measured by scanning the transmission frequency of the filter. Unlike Jpn. J. Appl. Phys., 33, pp. 3217-3219 (1994), an organism can be used as the measurement object in the present embodiment due to the use of pulse light in which the SN ratio reaches a maximum in a range that does not optically damage the organism, and capturing backward scattered light that is scattered at an angle of 90° or more.

What is claimed is:

1. An elasticity and viscosity measuring apparatus comprising:
    excitation light generating means for generating modulated excitation light;
    an optical system for focusing the excitation light to a focusing position on a measurement object and capturing scattered light generated by the measurement object;
    locally oscillated light generating means for generating locally oscillated light;
    multiplexing means for multiplexing the captured scattered light and locally oscillated light;
    optical detection means for photoelectrically converting the multiplexed light and generating a photoelectric current;
    a filter for selecting and extracting part of an AC component of the photoelectric current;
    frequency-selective power detection means for selecting and measuring, based on the electric power of the extracted photoelectric current, a frequency component related to modulating the excitation light; and
    analyzing means for calculating the light spectrum of the scattered light and obtaining at least one parameter selected from the strength of the scattered light, the frequency, and the linewidth based on the elastic waves in the measurement object; wherein
    the optical system selects and captures part of the scattered light that forms an angle of 90 degrees or greater in relation to the wave number vector of the excitation light.

2. The elasticity and viscosity measuring apparatus according to claim 1, further comprising
    focused position measuring means for measuring the focused position of the excitation light.

3. The elasticity and viscosity measuring apparatus according to claim 1, wherein
    the excitation light is a periodic pulse train; and
    the repetition frequency f, the duty ratio d, the light wavelength $\lambda$, and the average power P satisfy the following relationships:
    $f \geq 30$ kHz, $d \geq 0.2$, 700 nm$\geq\lambda$1100 nm, $P \geq 3.5$ mW.

4. The elasticity and viscosity measuring apparatus according to claim 1, wherein
    the excitation light is a pulse train with a repetition frequency $f_1$;
    the locally oscillated light is modulated in strength or polarization at a frequency $f_2$; and
    the frequency-selective power detection means selectively detects a frequency component at a frequency ($f_1$-$f_2$).

5. The elasticity and viscosity measuring apparatus according to claim 1, wherein
    the excitation light generating means and the locally oscillated light generating means share a single laser light source; and
    the transmission frequency of the filter is variable.

6. The elasticity and viscosity measuring apparatus according to claim 1, wherein
    the excitation light generating means and the locally oscillated light generating means have separate laser light sources;
    the frequency of at least one of the laser light sources is variable; and the apparatus comprises frequency difference measuring means for measuring the difference in optical frequencies between the excitation light and the locally oscillated light.

7. The elasticity and viscosity measuring apparatus according to claim 1, wherein the bandwidth of the filter is 10 MHz to 1 GHz.

8. The elasticity and viscosity measuring apparatus according to claim 1, wherein the bandwidth of the filter is variable; and the filter bandwidth can be adjusted to coincide with the Brillouin linewidth of the measurement object.

9. The elasticity and viscosity measuring apparatus according to claim 3, wherein the excitation light is a pulse train with a cyclic frequency $f_1$;

the locally oscillated light is modulated in strength or polarization at a frequency $f_2$; and the frequency-selective power detection means selectively detects a frequency component at a frequency $(f_1-f_2)$.

* * * * *

UNITED STATES PATENT AND TRADEMARK OFFICE
CERTIFICATE OF CORRECTION

PATENT NO. : 7,777,891 B2
APPLICATION NO. : 12/067439
DATED : August 17, 2010
INVENTOR(S) : Takemi Hasegawa It is certified that error appears in the above-identified patent and that said Letters Patent is hereby corrected as shown below:

Column 14, line 45, change the last line of Claim 3 from

"$f \geq 30$ kHz, $d \geq 0.2$, 700 nm $\geq \lambda 1100$ nm, $P \geq 3.5$ mW."

to

-- $f \geq 30$ kHz, $d \leq 0.2$, 700 nm $\leq \lambda \leq 1100$ nm, $P \leq 3.5$ mW. --

Signed and Sealed this

Nineteenth Day of October, 2010

David J. Kappos
*Director of the United States Patent and Trademark Office*